US010076593B2

(12) United States Patent
Woolford (10) Patent No.: US 10,076,593 B2
(45) Date of Patent: Sep. 18, 2018

(54) PRESSURE CONTROL ALGORITHM FOR HIGH RESISTANCE HARDWARE

(71) Applicant: Brady L. Woolford, Mapleton, UT (US)

(72) Inventor: Brady L. Woolford, Mapleton, UT (US)

(73) Assignee: Stryker Corporation, Kalamazoo, MI (US)

(*) Notice: Subject to any disclaimer, the term of this patent is extended or adjusted under 35 U.S.C. 154(b) by 181 days.

(21) Appl. No.: 15/153,845

(22) Filed: May 13, 2016

(65) Prior Publication Data

US 2016/0346443 A1    Dec. 1, 2016

Related U.S. Application Data

(60) Provisional application No. 62/166,198, filed on May 26, 2015.

(51) Int. Cl.
| | |
|---|---|
| *A61M 1/00* | (2006.01) |
| *A61M 5/48* | (2006.01) |
| *A61B 1/015* | (2006.01) |
| *A61B 1/317* | (2006.01) |

(52) U.S. Cl.
CPC ........... *A61M 1/0058* (2013.01); *A61B 1/015* (2013.01); *A61M 5/484* (2013.01); *A61B 1/317* (2013.01); *A61M 2205/3334* (2013.01)

(58) Field of Classification Search
CPC ...... A61M 1/0058; A61M 5/484; A61B 1/015
USPC ......................................................... 604/28
See application file for complete search history.

(56) References Cited

U.S. PATENT DOCUMENTS

| | | | |
|---|---|---|---|
| 5,460,490 | A | 10/1995 | Carr et al. |
| 6,162,194 | A | 12/2000 | Shipp |
| 7,273,359 | B2 | 9/2007 | Blight et al. |
| 7,287,968 | B2 | 10/2007 | Haser et al. |
| 7,371,224 | B2 | 5/2008 | Haischmann et al. |
| 7,510,542 | B2 | 3/2009 | Blight |
| 7,981,073 | B2 | 7/2011 | Möstam et al. |
| 8,206,342 | B2 | 6/2012 | Hacker et al. |
| 8,608,682 | B2 | 12/2013 | Möllstam et al. |
| 8,801,654 | B2 | 8/2014 | Möllstam et al. |
| 2013/0267779 | A1* | 10/2013 | Woolford ........... A61B 1/00039 600/156 |

* cited by examiner

*Primary Examiner* — Phillip Gray
(74) *Attorney, Agent, or Firm* — Flynn Thiel, P.C.

(57) ABSTRACT

A pump and pump controller which uses an algorithm to quickly achieve and maintain a set pressure in a surgical site when high resistance hardware is being used is provided. The algorithm uses a gravity control type loop and uses pressure loss calculations to quickly respond to changing joint conditions. A method of using such a pump and pump controller is also provided.

10 Claims, 4 Drawing Sheets

PRESSURE CONTROL ALGORITHM FOR HIGH RESISTANCE HARDWARE

CROSS REFERENCE TO RELATED APPLICATION

This claims the benefit of U.S. Provisional Application No. 62/166,198, filed May 26, 2015, the disclosure of which is hereby incorporated by reference in its entirety.

FIELD OF THE INVENTION

This invention relates generally to pump systems and, more particularly, to pumps and pump controlling devices and methods for surgical procedures.

BACKGROUND OF THE INVENTION

Fluid management pump systems are employed during surgical procedures to introduce sterile solution into surgical sites. One such procedure in which a fluid management pump is employed is during an endoscopic surgical procedure. In endoscopic surgery, an endoscope is inserted into the body at the site where the surgical procedure is to be performed. The endoscope is a surgical instrument that provides a view of the portion of the body in which it is inserted. Other surgical instruments are placed in the body at the surgical site. The surgeon views the surgical site through the endoscope in order to manipulate the other surgical instruments. The development of endoscopes and their companion surgical instruments has made it possible to perform minimally invasive surgery that eliminates the need to make large incisions to gain access to the surgical site. Instead, during endoscopic surgery, small openings, called portals, are formed in the patient. An advantage of performing endoscopic surgery is that since the portions of the body that are cut open are minimized, the portions of the body that need to heal after the surgery are likewise reduced. Still another advantage of endoscopic surgery is that it exposes less of the interior tissue of the patient's body to the open environment. This minimal opening of the patient's body lessens the extent to which the patient's internal tissue and organs are open to infection.

The ability to perform endoscopic surgery is enhanced by the development of fluid management pumps. A fluid management pump is designed to pump a sterile solution into the enclosed portion of the body at which the endoscopic surgical procedure is being performed. This solution expands and separates the tissue at the surgical site so as to increase both the field of view of the surgical site and the space available to the surgeon for manipulating the surgical instruments. One type of endoscopic surgery in which fluid management pumps have proven especially useful is in arthroscopic surgery. In arthroscopic surgery, a specially designed endoscope, called an arthroscope, is employed to examine inter-bone joints and the ligaments and muscles that connect the bones. A fluid management pump is often employed in arthroscopic surgery to expand the space between the bones and adjacent soft tissue in order to increase the field in which the surgeon can perform the intended surgical procedure. Fluid management pumps are, during arthroscopic surgery, used to increase the surgical view of the joints that form an elbow, a knee, a wrist, or an ankle. Fluid management pumps are used both in endoscopic surgery and in other surgical procedures to remove debris generated by the procedure.

A fluid management pump system includes a number of different components. There is the pump unit that supplies the motive force for pumping the sterile solution through an inflow tube into the surgical site. The actuation of the pump is regulated by a control unit. The control unit receives as input signals both surgeon-entered commands and an indication of the liquid-state fluid pressure at the surgical site. Still another component of a fluid management pump system is the tube set. The tube set includes the fluid communication tubes that are connected between the pump unit, the control unit, and the surgical site in the patient which is infused with the distention fluid. The tube set includes the previously described inflow tube through which the solution is introduced into the surgical site. There is also an outflow tube through which the solution and any waste material carried therewith are removed from the surgical site. Fluid flow from the site can be regulated by a valve integral with the control unit that selectively opens and closes the outflow tube. The tube set also includes a pressure feedback tube. The pressure feedback tube provides a fluid communication path between the surgical site and the control unit so that a pressure transducer integral with the control unit can monitor the fluid pressure at the surgical site. The pressure signal the transducer supplies is used by the control unit to regulate the actuation of the pump unit and to control the open/closed state of the fluid outflow tube.

Most fluid management pump systems further include cannulae that are inserted into the patient. The cannulae function as the actual fluid communication paths between the surgical site and the tubes forming the tube set. In order to minimize the number of portals that need to be formed in the patient, a single cannula can be provided that provides both the fluid communication into the body for the inflow tube and the pressure feedback tube that functions as the guide bore through which the endoscope is inserted. These particular cannulae are called pressure sensing cannulae.

Other advantages, objects and/or purposes of the invention will be apparent to persons familiar with constructions of this general type upon reading the following specification and inspecting the accompanying drawings.

DETAILED DESCRIPTION OF PREFERRED EMBODIMENTS

For purposes of description herein, it is to be understood that the invention may assume various alternative orientations, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
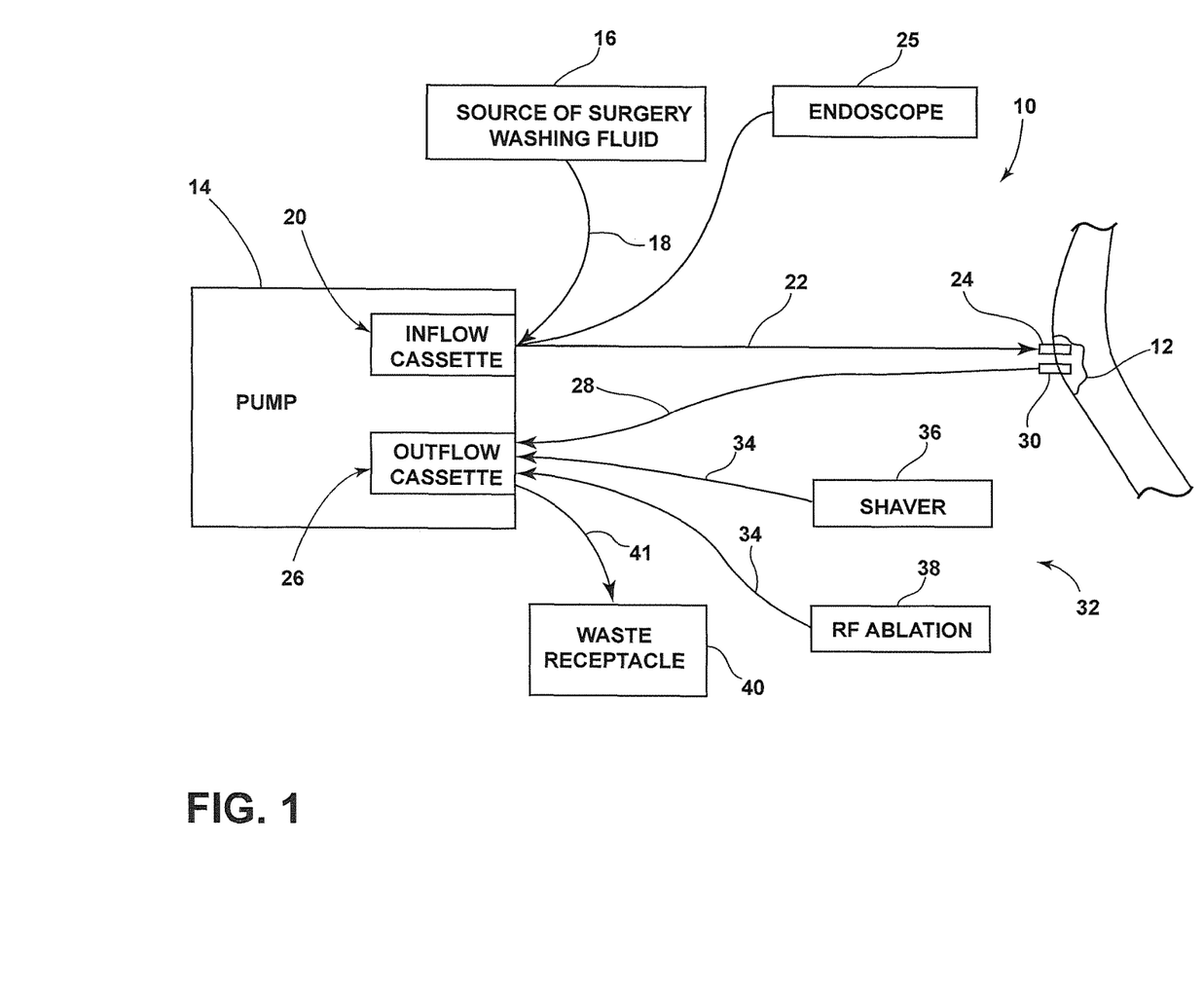
FIG. 1 is a schematic view of a pump system of the present invention illustrating flow paths through the pump system.

Referring to FIG. 1, there is illustrated a pump system 10 and flow paths through the pump system 10. The pump system 10 includes a pump 14 configured to provide a surgery washing fluid to a body cavity 12 (e.g., a joint) during surgery and to suction waste fluid out of the body cavity 12.

As illustrated in FIG. 1, the pump 14 receives a surgery washing fluid from a source of surgery washing fluid 16. The surgery washing fluid could be any washing fluid used in surgery and could be, for example, 0.9% saline or Ringer's lactate. The surgery washing fluid can provide irrigation to the body cavity 12, provide distension in a joint to give a surgeon room to operate in certain joints, and/or provide tamponade to help with bleeding. Input tubing 18 is connected between the source of surgery washing fluid 16 and the pump 14 for supplying the surgery washing fluid to the pump 14. As illustrated in FIG. 1, the pump 14 can have an inflow cassette 20 inserted therein for receiving the surgery washing fluid and for pushing the surgery washing fluid to the body cavity 12 through an inflow tube 22. Typically, the inflow tube 22 is inserted into and/or connected to an inflow cannula 24 inserted into the body cavity 12. An endoscope 25 may also be connected to the inflow cassette 20.

The illustrated pump 14 can also have an outflow cassette 26 inserted therein for suctioning the fluid out of the body cavity 12. An outflow tube 28 extends between the body cavity 12 and the outflow cassette 26, with the outflow tube 28 typically inserted into and/or connected to an outflow cannula 30 inserted into the body cavity 12. The outflow cassette 26 can also have one or more surgery devices 32 connected thereto by device suction tubing 34. The surgery devices 32 are configured to suction the fluid out of the body cavity 12 while the surgery devices 32 are being used within the body cavity 12. The surgery devices 32 can include a shaver 36, an RF ablation device 38 or any other surgery device that can suction waste fluid out of the body cavity 12. The outflow cassette 26 is connected to a waste receptacle 40 by waste tubing 41. The outflow cassette 26 works with the pump 14 to suction the waste fluid out of the body cavity 12 and to push the waste fluid into the waste receptacle 40 through the waste tubing 41. The input tubing 18, the inflow tube 22, the outflow tube 28, the device suction tubing 34, and the waste tubing 41 can have any length.

In the illustrated example, the pump system 10 can receive information from all elements of the pump system 10 to change the flow rate and/or pressure of the surgery washing fluid being provided to the body cavity 12 (i.e., inflow characteristics) and/or to change the flow rate and/or pressure of the waste fluid being suctioned from the body cavity 12 (i.e., outflow characteristics). In the illustrated example, the pump 14 and/or an integration system can contain an algorithm for altering the inflow and/or outflow characteristics. Therefore, while most of the information paths are illustrated as being between the pump 14 and other elements, the information paths could lead to the integration system instead of the pump 14. In some embodiments, the integration system is disposed within a pump housing. The pump 14 and/or integration system can include information from the body cavity 12 (e.g., pressure and temperature within the body cavity 12), the surgery devices 32 (e.g., the shaver 36 and/or the RF ablation device 38), a foot pedal, a remote control, inflow information measured within the pump 14 including pressure information of the fluid outputted from the pump 14, and outflow information measured within the pump 14 including pressure information of the fluid suctioned by the pump 14. The pump 14 can also include an input device for inputting information directly into the pump 14 (e.g., a keyboard or touch screen).

Figure 2:
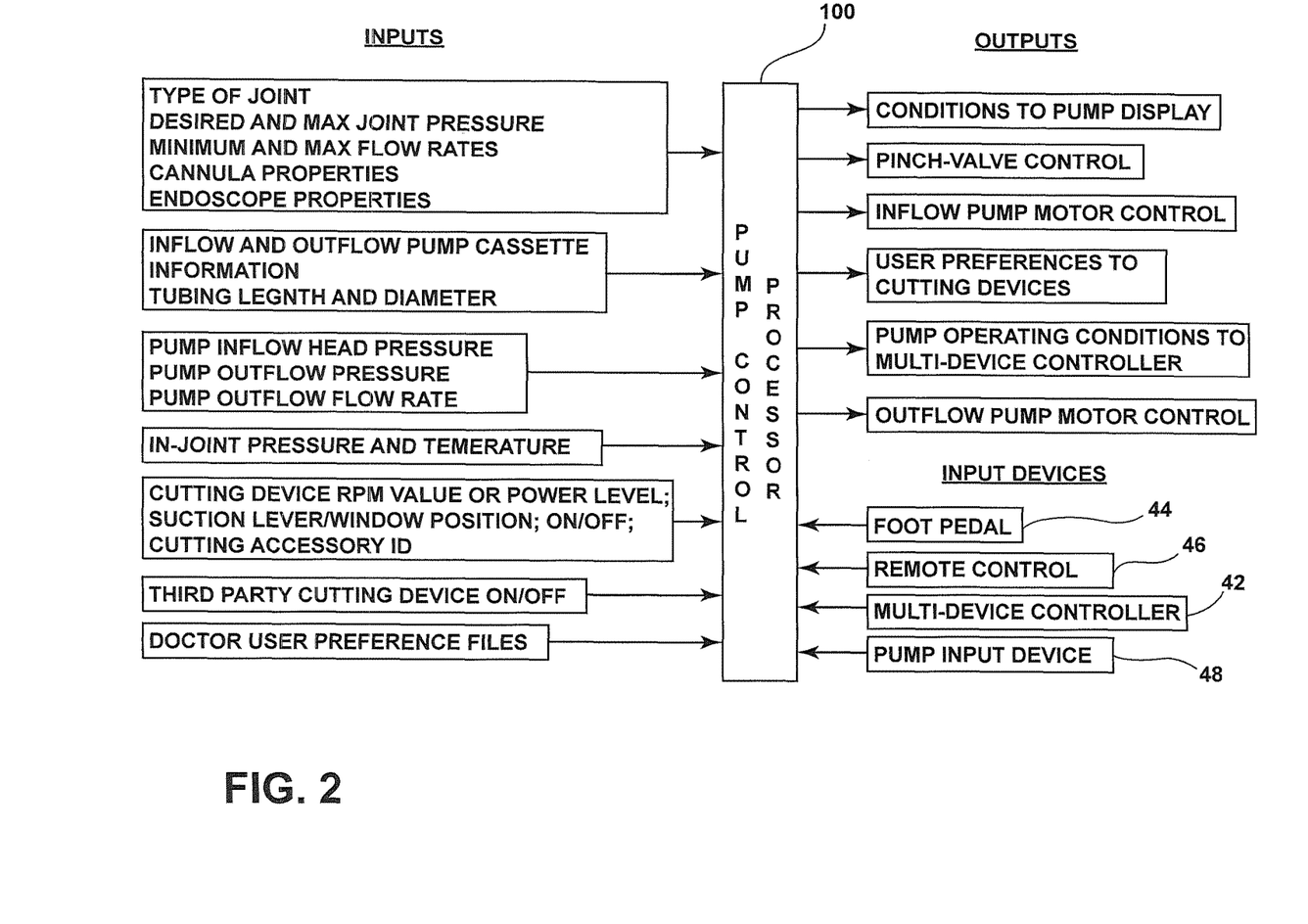
FIG. 2 is a block diagram showing inputs provided to the pump control processor and outputs from the pump control processor.

FIG. 2 illustrates various inputs, outputs and input devices that are provided with a pump control processor 100. The input devices include the multi-device operating room controller 42, a foot pedal 44, a remote control 46, and a pump input device 48.

In various embodiments, only some of the inputs shown in FIG. 2 are provided to the pump control processor 100 and only selected ones of the outputs are output therefrom. For example, in some embodiments of the invention there is no outflow pump motor control. In other embodiments, an unidentified third party surgical device is provided, wherein the pump control processor 100 does not know device parameters of such a surgical device. Many embodiments of the invention do not include an in-joint pressure sensor or an in-joint temperature sensor, and thus such directly measured joint pressure values are not provided to the pump control processor 100. In some embodiments, a multi-device operating room controller is not connected to the pump system 10. Further, additional inputs and outputs for the pump control processor 100 that are not shown in FIG. 2 are also contemplated.

In some embodiments, only inflow fluid flow control is provided by the pump 14 and the pump control processor 100 to initially maintain a constant desired in-joint pressure ($P_{joint}$) without the use of an in-joint pressure sensor. In other embodiments, inflow/outflow fluid control is provided by the pump 14 and the pump joint pressure is again maintained without an in-joint pressure sensor.

Identified Components:

In one embodiment, the type of inflow cannula 24, type of endoscope 25, and the type of inflow tube 22 and length thereof are identified. Identification information for each of the components is input into the pump control processor 100 manually or automatically. The dimensions and length of the inflow and outflow tubing, along with other properties, is typically automatically read by RF communication or identified by the pump control processor 100 when inflow and outflow tubing, via cassettes or otherwise, is inserted into the pump 14.

The pump control processor 100 utilizes stored or read dimensions and other values for the known identified components to calculate a pressure loss ($P_{loss}$) curve based on the dimensions and characteristics of the inflow tubing 22, the inflow cannula 24 and the endoscope 25 that define an inflow path to the surgical site 12 in the joint. Details for the inflow tubing, the endoscope 25 and the inflow cannula 24 can be stored in pump memory. An algorithm or program executed by the pump control processor 100 calculates coefficients ($COEF_1$ and $COEF_2$) defining the $P_{loss}$ curve from the properties including the dimensions and length of the tubing 22, and properties including dimensions of both the cannula 24 and the endoscope 25. The coefficients are provided in an equation including speed or velocity, typically revolutions per minute (RPMs) of an inflow pump motor to calculate a $P_{loss}$ value at a point on the $P_{loss}$ curve as defined for a given inflow pump motor speed.

Obtaining a $P_{loss}$ value on the $P_{loss}$ curve for an RPM value of the inflow pump motor requires an algorithm or program calculating a second order polynomial using the load coefficients $COEF_1$, $COEF_2$ as set forth in the following equation:

$$P_{loss} = COEF_1 \times (\text{RPM value})^2 + COEF_2 \times (\text{RPM value})$$

The above pressure loss equation results in a calculated $P_{loss}$ value at a given RPM value for the inflow motor of the pump system.

A measured head pressure ($P_{head}$) sensed by a pump inflow pressure sensor of the pump 14 disposed at or near the inflow pump cassette 20 may be used to calculate the in-joint pressure using the following equation:

$$P_{joint} = P_{head} - P_{loss}$$

Using the above calculation, the pump control processor 100 may control the inflow pump motor to maintain the $P_{joint}$ value at a generally constant predetermined desired pressure value regardless of the outflow arrangement.

The pump control processor 100 controls the inflow pump motor over a range in which there is a linear relationship between the flow rate and the inflow pump motor RPM value using the following equation:

$$\text{Inflow} = \text{COEF}_{INFL} \times (\text{RPM value})$$

The inflow coefficient $\text{COEF}_{INFL}$ value is loaded from a look-up table for the identified hardware (cannula, inflow tubing, etc.) connected to the pump.

In some embodiments, an inflow cannula provides fluid to a joint without an endoscope. In such an instance, the pump control processor 100 simply determines the load coefficients and inflow coefficient from the inflow tubing and the inflow cannula. In other embodiments the cannula is an outflow cannula or a different cannula.

Unidentified Components:

Another embodiment of an inflow pump control arrangement is utilized wherein the dimensions and other properties of the inflow tubing 22, inflow cannula 24, and the endoscope 25 are unknown. In this embodiment, the pump control processor 100 utilizes a calibration routine or an algorithm as a start-up pump priming routine to obtain data values that are used to calculate the pressure loss coefficients $\text{COEF}_1$ and $\text{COEF}_2$ that define a $P_{loss}$ curve. At start-up, the pump priming routine begins. Such a routine is described in U.S. patent application Ser. No. 13/782,660, filed Mar. 1, 2013, which published as U.S. Publication No. 2013/0267779, and which is hereby incorporated by reference in its entirety. The pressure loss equation thus results in a calculated pressure loss $P_{loss}$ for a pump system having an unidentified tubing size and length, an unidentified endoscope and an unidentified cannula disposed between the pump and the surgical site of a joint.

Unlike the first embodiment discussed above, wherein the hardware such as the endoscope, the cannula, and the tubing are identified, in this embodiment pump priming execution is necessary to determine the coefficients $\text{COEF}_1$, $\text{COEF}_2$ for the second order polynomial equation defining a $P_{loss}$ curve.

Unlike the first embodiment, wherein the inflow coefficient $\text{COEF}_{INFL}$ is determined from the identified hardware, $\text{COEF}_{INFL}$ is determined from a look-up table in view of the values of coefficients $\text{COEF}_1$, $\text{COEF}_2$. In some embodiments, properties of the inflow tubing 22 may be obtained by the pump control processor 100 from the inflow pump cassette before start-up.

Recognized Surgical Device:

Surgical devices 32 manufactured by the manufacturer of the pump system 10 recognize each other's signals and thus are capable of two-way communication. Thus, performance parameters of surgical devices 32 and cutting accessories can be communicated to the pump control processor 100. In some embodiments for a shaver 36, parameters including shaver identification information and identification information including the type and size of bur or other surgical device accessory disposed on the shaver is provided automatically to the pump control processor 100. Further, the ON/OFF condition, the specific cutter or bur used, the type of operating mode selected for the shaver (examples are Forward, Reverse, Oscillation, etc.), the real-time RPM value of a shaver motor during operation, and other properties can be provided to the pump control processor 100 via the communication bus to optimize the performance of the pump 14. Further, a window size and window position of a surgical device and/or cutting accessory can be provided to the pump control processor 100.

With regard to an RF ablation device, parameters such as identification information for an RF handpiece, the ON/OFF condition thereof, the type of RF probe, identification information for the probe including suction and non-suction parameters, and the RF power level output setting can be provided automatically to the pump control processor 100 for optimizing operation of the pump 14.

In some embodiments, the dimensions of a flow path through a surgical device handpiece and the position of a lever controlling flow through the path can be provided over the communication bus to the pump control processor 100. In some embodiments surgical device identifiers and cutting accessory identifiers are sent over the communication bus to the pump control processor 100 and values for the bur size, window size, and flow path dimensions that are previously stored in the pump memory can be retrieved.

Figure 3:
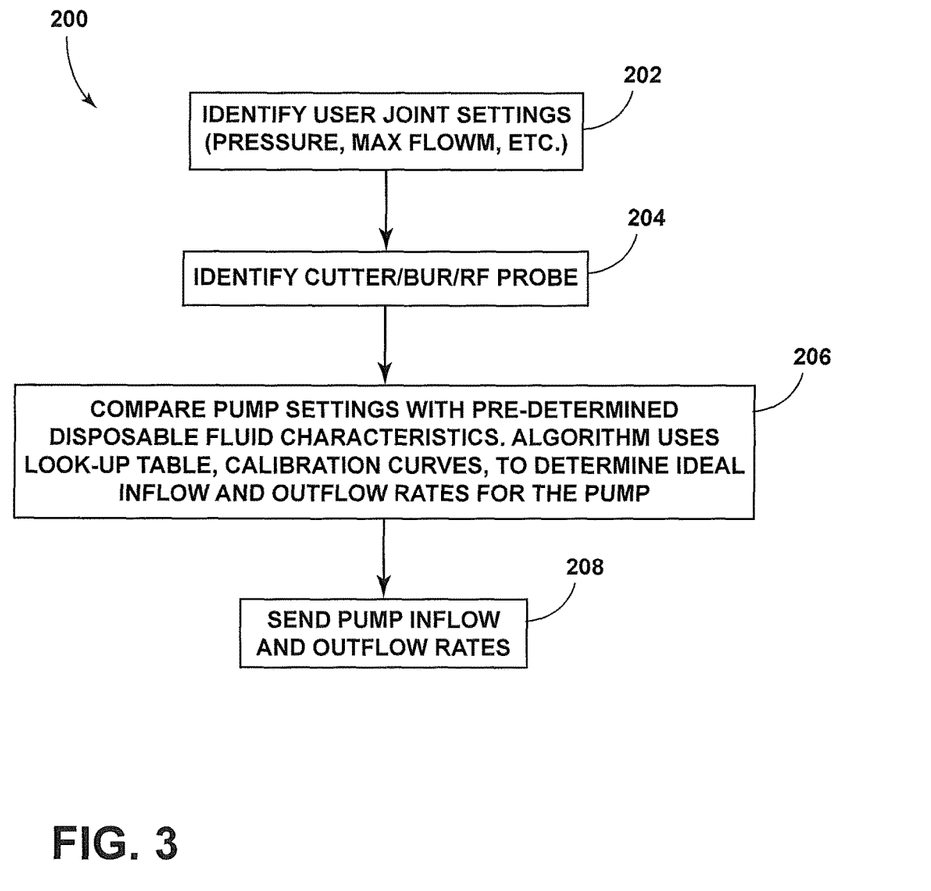
FIG. 3 is a flowchart of a portion of a pump system operating routine that includes obtaining information regarding a cutting accessory.

FIG. 3 is a flowchart of the steps of a portion of a pump flow control routine 200 executed by the pump control processor 100 that emphasizes the identification of a cutting accessory. At step 202, the type of joint, maximum and minimum flow rates, a desired or best flow rate that minimizes fluid consumption and maintains good visibility, a maximum pressure value, a desired pressure value and other types of information, including but not limited to the information or parameters listed and shown in FIG. 2, can be provided to the pump control processor 100. The information can be manually entered into the pump control processor 100 via an input device, read or downloaded automatically from a memory card or the like, or provided by other means. Then the routine advances to step 204.

At step 204 surgical device information, including identification information for a cutting accessory attached thereto, is provided to the pump control processor 100. As discussed above, the information can be provided over a communication bus. The surgical device 32 can include an RF reader to identify an RF tag secured to the cutting accessory. In another embodiment, the pump includes an RF reader to identify RF tags secured to both the surgical device and the cutting accessory. The routine then advances to step 206.

At step 206, the routine or program executed by the pump control processor 100 compares pump settings with predetermined disposable fluid flow characteristics. An algorithm or program uses a look-up table, calibration curves, and in some embodiments additional information to determine ideal fluid inflow and fluid outflow rates for operation of the pump 14. At step 208, the pump inflow control signals, and in some instances outflow information, is provided to the inflow pump motor and to additional devices to obtain ideal in-joint pressures and fluid flow at the surgical site.

A feedback path (not shown) from step 208 returns to a program or routine whereat an algorithm recalculates pump flow rates based on one or more of real-time joint pressure, inflow head pressure, pump motor speeds, surgical device speed, and ON/OFF condition. Typically, the routine does not need to re-identify the surgical device or the cutting accessory. Further, the user joint settings, such as desired joint pressure, maximum and minimum joint pressure, maximum and minimum fluid flow through the joint, and desired fluid flow information typically do not change, and thus the routine typically does not return to step 202 until one cutting operation ends and another cutting operation begins.

In one example, for a shaver operating at a motor speed of 12,000 RPM with a 5.0 mm round bur attached thereto, and a desired pressure value of 70 mmHg, the algorithm or routine executed by the pump control processor 100 provides outputs to the inflow pump motor, the outflow pump motor, and in some instances to other devices including outflow pinch valves, to obtain the desired joint pressure of 70 mmHg, while maintaining desirable inflow and outflow rates for the pump output.

When the shaver 36 is operated, the pump control processor 100 receives the ON/OFF condition and the RPM output value of the shaver and calculates and controls the inflow pump RPM value that is output by the inflow pump motor, controls the outflow pump motor, and controls pinch valves provided with or near an outflow cassette by opening a valve for the outflow tubing 34 connected to the shaver while closing a separate outflow tubing 28 from the outflow cannula 30.

The additional surgical device information, along with the joint pressure values calculated or sensed as described above, enable the pump control processor 100 of the pump 14 to more accurately control the $P_{joint}$ value and fluid flow rates that result in surgical site conditions that closely correspond to the selections or inputs of an authorized medical user operating the pump system 10.

As the shaver is identified, a non-linear outflow rate to RPM curve is provided with a look-up table containing coefficients to predict the outflow rate based on the outflow RPM for controlling the pump to provide a desired or best outflow rate. This is also the procedure for a recognized RF probe.

User preferences and other information from the pump control processor 100 can be provided to the surgical device 32, such as the shaver 36 and RF ablation device 38. The preferences can include surgical device settings preferred by the medical user that will be operating the surgical device 32 and the pump system 10.

Unrecognized Shaver and RF Ablation Surgical Devices:

The pump 14 can be utilized with unrecognized third-party surgical devices 32 that are not identifiable by the pump control processor 100. Such RF ablation devices and shaver devices are typically connected to power outlets located on the backside of the pump housing. Located within the pump housing are current and/or voltage sensing devices that sense a current waveform of the power drawn by the unrecognized surgical devices when operated. Instantaneous and past changes in the current waveform can be normalized to changes in the applied mains voltage and the pump control processor 100 can execute a linear-discrimination algorithm to optimally differentiate between times when the unidentified surgical devices are off and when the surgical devices are activated to treat or cut tissue.

As discussed above, the critical flow rate values and maximum pressure value for the surgical site 12 at the joint are typically different during operation of a surgical device 32 as compared to during non-operation of the surgical device. Therefore, sensing surgical device activation enables adjustments to the desired joint pressure value and fluid flow by control of the inflow pump motor, outflow pump motor and other devices while the surgical device is activated.

In-Joint Sensor:

In some embodiments an in-joint sensing device includes an in-joint pressure sensor and/or an in-joint temperature sensor that are disposed at or adjacent the surgical site. The in-joint sensing device can obtain and send a real-time pressure value from the surgical site 12 to the pump control processor 100, thereby avoiding reliance on the calculated $P_{loss}$ curves discussed above. The in-joint sensing device also reduces time delay in determining pressure changes in the joint. For instance, when pressure changes are measured upstream, there is a delay in the pressure change at the joint propagating through the inflow tubing to the sensor in the pump 14. The in-joint pressure sensor also removes the upstream pressure measuring influence of hydrostatic head which occurs due to height differences between the pump and the cutting accessory located at the surgical site. Therefore, the pump need not be maintained at the same level or height as the surgical site.

Overpressure:

Regardless of the type of $P_{joint}$ calculation or direct pressure measurement, a $P_{joint}$ value must not exceed a predetermined pressure value. Thus, when an overpressure condition is calculated or measured, the pump control processor 100 performs at least one of operating outflow pinch valves, reducing the RPM value of the inflow pump motor, and other steps to reduce the joint pressure.

Figure 4:
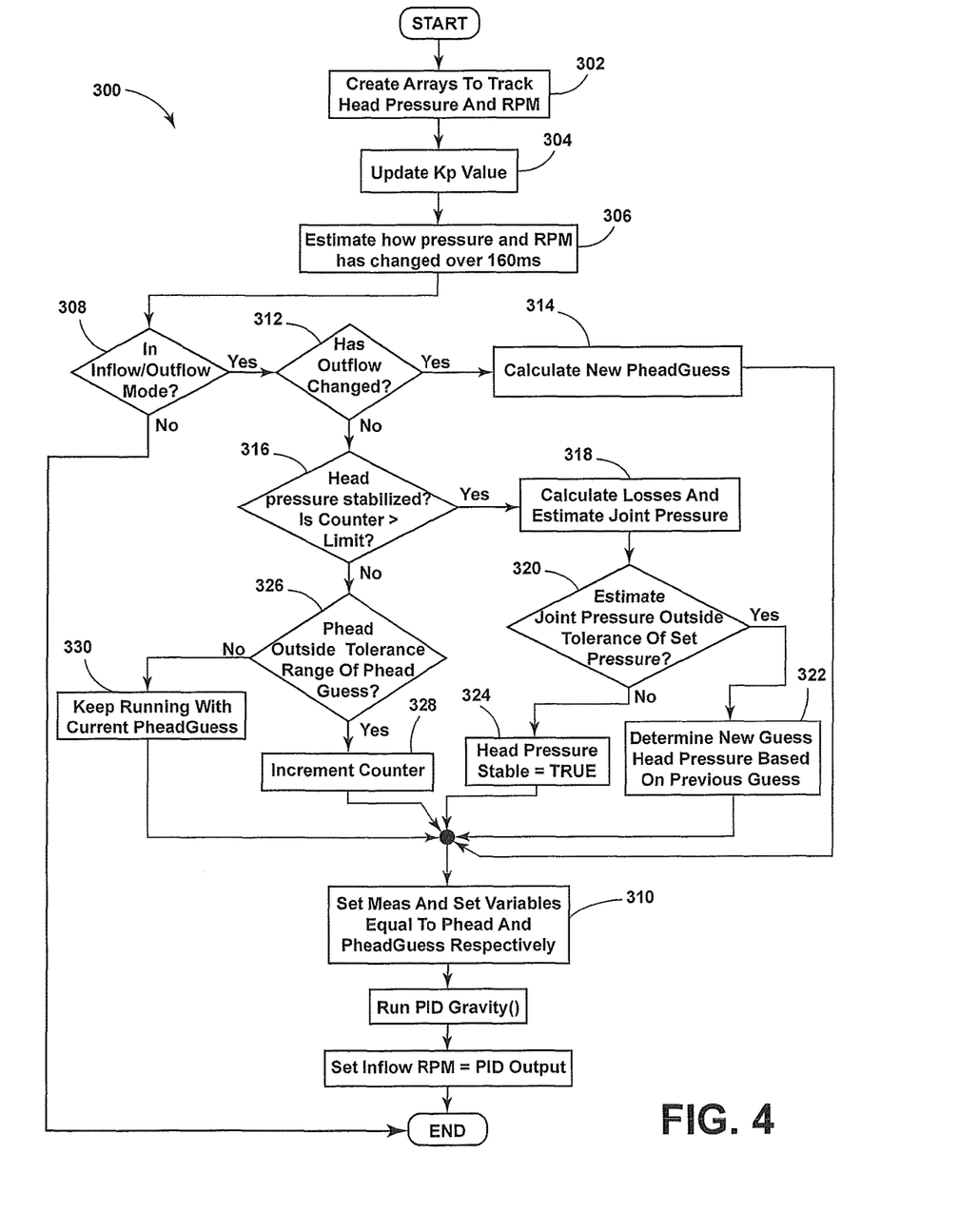
FIG. 4 is a flowchart of a portion of a pump system operating routine to adjust the head pressure in a surgical pumping system.

Adjustment of Pump Head Pressure in High Pressure Loss Situations:

An algorithm 300, illustrated in FIG. 4, may be used to adjust the head pressure of the pump 14 during a resection procedure. This algorithm, while not limited to such situations, is especially useful when high resistance hardware is being used such as for small joint arthroscopy procedures. The algorithm functions by taking an initial guess at what the pressure head value should be in order to provide the desired pressure in the surgical site (similar to a gravity control-type loop), for example a joint, that has been set by the user. A PID control loop is used to quickly adjust the inflow motor RPMs until the measured head pressure attained is within a set tolerance of the guessed head pressure. Once this pressure is attained, a pressure loss curve for the specific hardware in use is employed to calculate the pressure losses. The losses are subtracted from the head pressure to determine the estimated surgical site pressure. The estimated surgical site pressure is compared to the set pressure and if the estimated surgical site pressure is outside of an acceptable tolerance then an iterative approach is used to guess what the next head pressure value should be in order to provide the desired set pressure of the surgical site. This process of guessing the head pressure, calculating the losses, and comparing the estimated surgical site pressure is continued until the estimated surgical site pressure is within the tolerance of the desired set pressure. The algorithm can also use information about the outflow fluid conditions in order to improve the guess of what the head pressure should be in order to hit and maintain the set pressure.

After the algorithm 300 is started, one or more arrays are created to record and track data with regard to pressure and RPM values in step 302. The algorithm then proceeds to step 304 at which the $K_p$ value, used to drive the controller, is updated. Moving to step 306, the algorithm estimates how the pressure value and the RPM value has changed over the previous 160 milliseconds. This is preferably done by comparing the current number to the last four measurements, which are taken every 40 milliseconds. After the estimates of the change in pressure and RPM values are determined, the algorithm proceeds to step 308 at which the algorithm determines whether the system is in an Inflow/Outflow mode. If the answer is NO, the algorithm proceeds to the END and the routine is exited.

If the system is in the Inflow/Outflow mode (i.e., the answer to decision step 308 is "YES"), the algorithm then moves to step 312 at which is determined whether the outflow has changed. If the outflow has changed (i.e., the answer at step 312 is "YES"), then the algorithm moves to step 314 at which an initial or new $P_{head}$Guess is calculated and the algorithm proceeds to step 310, which is discussed in more detail below. If the outflow has not changed (i.e., the answer at decision step 312 is "NO"), the algorithm proceeds to step 316 which is another decision step. At step 316, it is determined whether the head pressure is stabilized, and whether the counter is over the counter limit. If the answer to both of these questions is satisfied (i.e., the answer to this decision is "YES"), the algorithm then moves to step 318.

At step 318 the pressure losses are calculated based on a pressure loss curve associated with the specific hardware being used. The pressure loss curves for various hardware devices are hard coded into the software. The joint pressure is also estimated at step 318. Once the pressure losses and joint pressure are calculated/estimated, the algorithm then proceeds to step 320, at which it is determined whether the estimated joint pressure is outside of the tolerance of the set pressure. If the estimated joint pressure is outside of the tolerance level of the set pressure (i.e., the answer to decision step 320 is "YES"), the algorithm then proceeds to step 322 at which a new $P_{head}$Guess is determined based on the previous $P_{head}$Guess, and the algorithm moves to step 310. If the estimated joint pressure is not outside of the tolerance of the set pressure (i.e., the answer to the decision step of 320 is "NO"), then the algorithm proceeds to step 324 at which the head pressure stability is set to TRUE and the algorithm then moves to step 310.

If the answer to the decision step 316 is "NO" (i.e., the head pressure is not stabilized or the counter is not over the counter limit, or both), then the algorithm proceeds to step 326 which is a decision step. At step 326 it is determined whether the $P_{head}$ value is outside of the tolerance range of the $P_{head}$Guess. If the $P_{head}$ value is outside of the tolerance range of the $P_{head}$Guess (i.e., the answer to the decision at step 326 is "YES"), then the algorithm proceeds to step 328 at which the counter is incremented and the algorithm moves to step 310. If the $P_{head}$ value is not outside the tolerance range of the $P_{head}$Guess (i.e., the answer to the decision at step 326 is "NO"), then the algorithm moves to step 330 at which the algorithm maintains the current $P_{head}$Guess value and the algorithm then moves to step 310.

At step 310, a MEAS variable is set to the $P_{head}$ value and a SET variable is set to the $P_{head}$Guess value. The MEAS and SET variables are used in the PID control loop to control the pressure. Upon completion of these values being set, the PID gravity tool, that is, a PID control algorithm used to set the inflow RPM value, is run and the inflow RPM is set to the PID output value. The algorithm is then at its end.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A method of controlling a surgical pump, the method comprising:
   providing a surgical pump having an inflow motor which performs within a range of RPMs for providing fluid to a surgical site;
   providing a pump controller connected to the surgical pump and which at least in part assists in controlling the surgical pump;
   providing surgical hardware to be used for a specific surgical procedure to be performed;
   providing a desired surgical site pressure value which is communicated to the pump controller;
   providing a set tolerance level for a $P_{head}$ value;
   the pump controller calculating a pressure loss value using a pressure loss curve for the surgical hardware;
   the pump controller estimating a value of the $P_{head}$ in order to achieve the desired pressure at the surgical site thereby creating a $P_{head}$ value;
   the pump controller adjusting the inflow motor RPMs;
   the pump controller subtracting the pressure loss value from the $P_{head}$ value to determine an estimated surgical site pressure value;
   the pump controller comparing the estimated surgical site pressure value with the desired surgical site pressure value;
   if the $P_{head}$ value is not within the set tolerance level, using an iteration to estimate an adjusted $P_{head}$ value and returning to the steps of the pump controller calculating a pressure loss value, the pump controller estimating a value of the $P_{head}$, the pump controller adjusting the inflow motor RPMs, and the pump controller subtracting the pressure loss value from the $P_{head}$ value; and
   if the $P_{head}$ value is within the set tolerance level, setting the $P_{head}$ value based on the comparison of the estimated surgical site pressure to the desired surgical site pressure value.

2. The method of claim 1, wherein if the head pressure is not stabilized and the head pressure is not outside of a tolerance range, the current head pressure guess value is maintained.

3. The method of claim 1, wherein only if the head pressure is stabilized and a counter value is greater than a predetermined counter limit value, the pump controller calculates the pressure loss value using the pressure loss curve.

4. The method of claim 1, wherein the pump controller estimates change in surgical site pressure and change in pump RPMs to use as a basis for calculating a new estimated $P_{head}$ value.

5. The method of claim 1, wherein the pump controller estimates an initial value of the head pressure and adjusts the inflow motor RPMs until the estimated initial value of the head pressure is obtained only if the system is in the Inflow/Outflow mode.

6. The method of claim 1, wherein if the head pressure is not stabilized and the head pressure is outside of a tolerance range, a counter is incremented and variables equal to the $P_{head}$ value and estimated $P_{head}$ value are set.

7. A method of controlling pressure in a surgical site, the method comprising:
   providing a surgical pump having an inflow motor for providing a flow of fluid to a surgical site;
   providing a pump controller connected to the surgical pump, which at least in part assists in controlling the surgical pump, the pump controller receiving information of inflow characteristics and outflow characteristics;
   providing surgical hardware for use in a specific surgical procedure to be performed;

the pump controller adjusting or maintaining the flow of fluid to a surgical site by performing the following steps:
(a) determining whether the outflow rate has changed,
(b) if the outflow rate has changed, calculating a $P_{head}$Guess value, and proceeding to step (e) below,
(c) if the outflow rate has not changed, calculating a pressure loss value using a pressure loss curve and estimating the pressure in the surgical site using the pressure loss value,
(d) determining a new $P_{head}$Guess value based on the previous $P_{head}$Guess value,
(e) providing variables which can be changed to correspond to $P_{head}$ and/or $P_{head}$Guess values,
(f) setting variables equal to the $P_{head}$ value and $P_{head}$Guess value, and
(g) setting an inflow RPM value for the surgical pump based on the $P_{head}$ and $P_{head}$Guess variables.

8. The method of claim 7, wherein if the head pressure is not stabilized and the head pressure is not outside of a tolerance range, the current $P_{head}$Guess value is maintained.

9. The method of claim 7, wherein the pump controller estimates the changes in surgical site pressure and pump RPMs to use as a basis for calculating a $P_{head}$Guess value.

10. The method of claim 7, wherein the pump controller determines an initial $P_{head}$Guess value and adjusts the inflow motor RPMs until the $P_{head}$Guess value is obtained only if the system is in an Inflow/Outflow mode.

* * * * *